United States Patent
Gimenez Calbo (10) Patent No.: US 9,756,796 B2
(45) Date of Patent: Sep. 12, 2017

(54) DEVICE FOR MEASURING PRESSURE AND CONTROLLING A FLOW

(71) Applicant: EMPRESA BRASILEIRA DE PESQUISA AGROPECUARIA - EMBRAPA, Brasilia - DF (BR)

(72) Inventor: Adonai Gimenez Calbo, Sao Carlos (BR)

(73) Assignee: EMPRESA BRASILEIRA DE PESQUISA AGROPECUÁRIA-EMBRAPA, Brasilia (BR)

( * ) Notice: Subject to any disclaimer, the term of this patent is extended or adjusted under 35 U.S.C. 154(b) by 47 days.

(21) Appl. No.: 14/369,264

(22) PCT Filed: Dec. 27, 2012

(86) PCT No.: PCT/BR2012/000538
§ 371 (c)(1),
(2) Date: Nov. 17, 2014

(87) PCT Pub. No.: WO2013/097011
PCT Pub. Date: Jul. 4, 2013

(65) Prior Publication Data
US 2015/0059866 A1 Mar. 5, 2015

(30) Foreign Application Priority Data
Dec. 30, 2011 (BR) ..................................... 1107358

(51) Int. Cl.
*F16K 17/36* (2006.01)
*A01G 25/16* (2006.01)
(Continued)

(52) U.S. Cl.
CPC ............... *A01G 25/16* (2013.01); *A01G 7/00* (2013.01); *G01D 5/02* (2013.01); *G01L 1/02* (2013.01);
(Continued)

(58) Field of Classification Search
USPC ............ 239/67; 47/1.01 R, 48.5; 73/37.5, 73
See application file for complete search history.

(56) References Cited

U.S. PATENT DOCUMENTS 2,416,664 A * 2/1947 Ruge ......................... G01B 7/16
33/790
3,470,737 A * 10/1969 Fridley .................... G01N 3/40
73/81
(Continued)

FOREIGN PATENT DOCUMENTS

WO 98/33037 A1 7/1998

OTHER PUBLICATIONS

International Search Report for PCT/BR2012/000538 dated Feb. 20, 2013.

*Primary Examiner* — R. K. Arundale
(74) *Attorney, Agent, or Firm* — Sughrue Mion, PLLC (57) ABSTRACT

A pressure measuring and flow-rate controlling device includes: a flattening plate including a fluid cavity in the flattening plate; a flexible contact membrane provided on said flattening plate; a support member configured to secure the flattening plate against a sample; a pressure adjuster; an inlet tube connected to the pressure adjuster at a first end of the inlet tube, the inlet tube connected to a first end of the fluid cavity at a second end opposite to the first end of the inlet tube; and an outlet tube connected to a second end opposite of the first end of the fluid cavity, where the
(Continued)

pressure adjuster is configured to control a flow rate of a fluid passing through the fluid cavity based on cell pressure of the sample.

10 Claims, 4 Drawing Sheets

(51) Int. Cl.
    *A01G 7/00*     (2006.01)
    *G01L 1/02*     (2006.01)
    *G01D 5/02*     (2006.01)
    *G05D 7/01*     (2006.01)
    *G01N 3/12*     (2006.01)

(52) U.S. Cl.
    CPC ............. *G05D 7/0113* (2013.01); *G01N 3/12* (2013.01); *Y10T 137/1842* (2015.04); *Y10T 137/2541* (2015.04)

(56) References Cited

U.S. PATENT DOCUMENTS

| | | | | |
|---|---|---|---|---|
| 3,688,309 A * | 8/1972 | Volberg | ............. | G01N 33/0098 324/692 |
| 3,747,399 A * | 7/1973 | Treirat | ............. | G01N 7/10 239/63 |
| 4,055,200 A * | 10/1977 | Lohoff | ............. | A01G 25/167 137/624.11 |
| 4,380,169 A * | 4/1983 | Graham | ............. | G01N 21/251 73/73 |
| 4,638,594 A | 1/1987 | Huguet et al. | | |
| 5,224,769 A * | 7/1993 | Holbrook | ............. | G01N 27/223 324/664 |
| 5,372,030 A * | 12/1994 | Prussia | ............. | A61B 3/165 209/509 |
| 5,691,473 A * | 11/1997 | Peleg | ............. | G01N 3/32 209/599 |
| 5,918,266 A * | 6/1999 | Robinson | ............. | G01N 3/12 209/599 |
| 5,956,897 A * | 9/1999 | Takashima | ............. | A01G 31/00 47/1.01 R |
| 6,240,766 B1 * | 6/2001 | Cawley | ............. | G01N 3/48 73/12.01 |
| 6,643,599 B1 * | 11/2003 | Mohr | ............. | G01N 3/42 702/108 |
| 6,701,665 B1 * | 3/2004 | Ton | ............. | A01G 1/00 47/17 |
| 6,892,900 B2 * | 5/2005 | Drechsel | ............. | F16K 7/063 137/487.5 |
| 7,316,322 B2 * | 1/2008 | Kawabata | ............. | G01N 21/359 209/509 |
| 7,994,802 B2 * | 8/2011 | Osypka | ............. | A01G 7/00 324/692 |
| 2004/0139650 A1 * | 7/2004 | Haq | ............. | A01G 27/006 47/48.5 |
| 2010/0018295 A1 * | 1/2010 | Kunze | ............. | A01G 7/00 73/64.45 |

\* cited by examiner

DEVICE FOR MEASURING PRESSURE AND CONTROLLING A FLOW

CROSS REFERENCE TO RELATED APPLICATIONS

This application is a National Stage of International Application No. PCT/BR2012/000538 filed Dec. 27, 2012, claiming priority based on Brazilian Patent Application No. PI 1107358-6, filed Dec. 30, 2011, the contents of all of which are incorporated herein by reference in their entirety.

FIELD OF THE INVENTION

The invention relates to a system for measuring cell turgor pressure, which functions like a dendroturgometer, for measuring the turgor pressure of stems, and also as a firmness-meter measuring the firmness of fruits and vegetables, and may be applied in conditions of field, laboratory, greenhouse, among others. The system takes advantage of the pressure and volumetric elasticity of the plant stem to obtain a hydric response and provide the reading of cellular turgescency, and the pressure reading is made by continuously acquiring data. For automation of drippers with flow-rate controlled by cell turgescency, the dropping is completely obstructed whenever the cell turgescency pressure becomes higher than the pressure of water entering the dripper. In order to read the cell turgescency pressure in after-harvest condition on said firmness-meter, the squeezing force may applied either manually on a portable instrument or by mechanically on a stationary instrument.

BACKGROUND OF THE INVENTION

An efficient irrigation system requires precise information on the specific needs of plants in different stages of development, under different climatic conditions. Many techniques are known, as for instance moisture sensors that are used for measuring moisture in the soil directly (tensiometers). However, controlling irrigation according to the needs of the plant (by measuring the turgor, which is controlled by plant transpiration), would be much more effective than irrigating in accordance with the value of water tension in the soil, since tensiometers may present disadvantages, failing to measure correctly if they do not have constant maintenance, this being one of the main obstacles for automation, besides the variation obtained in soils that have different textures, which often does not correspond to the reality of the need for water for the plant.

The turgor pressure of a plant is known as the difference in pressure between the inside and the outside of the cell wall. For a given cellular content in solutes the turgor pressure decreases as the hydric potential of the cell decreases (it becomes more negative). The more reliable information on the state of the water can be obtained if the turgor pressure in the plant cells is measured directly. Various types of devices for measuring turgor pressure have already been described. The reference instrument for measuring the turgency pressure of plant cells is the cellular pressure probe (Husken et al, Plant Physio. V. 61, p. 158-163, 1978). In this system, a microcapillar filled with low-viscosity mineral oil, is introduced into the cell. The water/oil meniscus is pushed backward and the cell turgescency pressure is then measured right after moving the water/oil meniscus back to the initial position by applying the necessary increase in cell pressure with the aid of a plunger.

Another reference method is using the thermoelastic probe of document PI9906212-7, which measures the expandability and compressibility of liquids for measuring the cell turgor pressure. In this system, the fluid used is a low-viscosity mineral oil contained in a capillary with a hermetically sealed bulb at the base. The system functions as a sensor on which one measures the pressure by raising the temperature so as to cause the meniscus formed on the oil/water interface and close to the capillary end to return to the initial reference position, and then the cell turgor pressure is measured. In addition to the turgor pressure, the thermoelastic probe enables measurements, by simple contact, of negative pressures inside the xylem vessels and even of negative pressures in cells of the intact dermal tissue (Calbo & Pessoa, R. Bras. Fisiol. Veg. v. 11, p. 129-136, 1999; Pessoa & Calbo, Eng. Agric., V. 21, p. 210-217, 2001).

The traditional cell pressure probe of Husken et al (1978) and the thermoelastic probe of document BR9906212-7 are, however, laboratory instruments for use under a microscope, for which reason they do not have handiness suitable for routine and rapid applications, which are necessary for pre- and post-harvest evaluations of ripening, senescence and hydration of fruits and vegetables. Additionally, one does not find applications for automation of irrigation systems so as to meet the hydric demands of crops.

The practical methods for evaluating firmness, on the other hand, have involved mechanical simulations of man's impressions while handling, biting, scratching, touching, piercing and breaking the products to be evaluated. Among the methods for evaluating firmness are: (a) penetration force of pointrs (Journal of The American Society for Horticultural Science, v. 103, p. 70-73, 1978); (b) measurement of linear deformation caused by a specified force or measurement of the force necessary to cause a specified linear deformation (HortScience, v. 8, 391-392, 1973); (c) measurement of the organ surface flattened by application of a known force or a force necessary to smash a specified area (Vitis, V. 20, p. 15-21, 1981; Scientia Horticulturae, v. 25, p. 129-136, 1985; Horticultura Brasileira, 12:14-18, 1995), herein called flattening method.

The measurement of the cell pressure of vegetables by flattening, without introducing capillaries inside it, has already been achieved by microsphere tonometry, as described in document U.S. Pat. No. 6,277,637. In this system, a glass microsphere is pressed against a dermal cell by applying a known force, the contact area being determined according to the flat diameter of the cell against the microsphere with the aid of a microscope. The ratio between the applied force and the flattened area is an estimate of the cell turgor pressure, in case the dermal cell has thin and flexible cells. Microsphere tonometry, just as the microcapillary cell-pressure probes, is a little practical microscopic and laboratory method.

The quantitative evaluation of the firmness may also be made with instruments that analyze various other physical properties. Thus, for instance, one has developed instruments like that of document U.S. Pat. No. 6,643,599, on which a pointer is used under constant force or under constant velocity, while interacting and perforating the organ. This is an instrument that generates accurate results, but that are not specifically related to cell turgescency.

Bernstein & Lustig (Vitis, v. 20, p. 15-21, 1981; Scientia Horticulturae, v. 25, p. 129-136, 1985) were pioneers in using the flattening method to measure the turgor pressure in grapes and in other juicy fruits, but that could be treated as a sphere involved by a membrane. Calbo & Calbo (Revista Brasileira de Fisiologia Vegetal, v. 1, p. 41-45, 1989)

extended the fundamentals of this method so that they could also be used for convex organs with regular and parenchymatous dermal tissue, as is the case of a great part of fruits and vegetables. Later, simple models of flatteners and a procedure for evaluating the flattened area by using a caliper rule were developed (Horticultura Brasileira, v. 12, p. 14-18, 1995).

The reversible and irreversible cellular deformations during measurements of firmness by the flattening method were evidenced subsequently (Horticultura Brasileira, v. 76, p. 365-370, 1995); Pesquisa Agropecuária Brasileira, v. 35, p. 2429-2436, 2000) and a few mathematical relations between cell turgor pressure and flattening pressure, according to the fraction of intercellular gaseous volumes in the tissues, were established by Calbo & Nery (Brazilian Archives of Biology Technology, v. 44, p. 41-48, 2001). The flattening method, as described by Calbo & Nery (Horticultura Brasileira, v. 12, p. 14-18, 1995) and by the other similar techniques considered in this paragraph, served only to measure the firmness of convex organs with the regular and parenchymatous dermal tissue. Thus, organs with irregularities and segmented organs of those with irregularities, in a practical way, can hardly be measured through instruments.

With the flattening method (Horticultura Brasileira, v. 12, p. 14-18, 1995), one can follow the loss of firmness caused by dehydration of various products, such as tuberous routs, tubercles and fruits. These measurements may be repeated on the same organ, without damaging it, and so this method has been used for selecting genotypes in vegetable improvement programs. Thus, Andrade et al (Pesquisa Agropecuária Brasileira, v. 40, p. 555-561, 2005), have developed a criterion determining the half-life of preservation of tomato fruits with a view to select cultivars with greater storage capability. The formula used in this and in other studies guided by Prof. Wilson Maluf at the Universidade Federal de Lavras (Federal University of Lavras) in Brazil is of the type:

$$Y = B + A(\tfrac{1}{2})^{-t/t_{1/2}} \qquad (\text{eq. 1}),$$

Wherein Y is the turgor pressure or firmness by flattening; B is a basal or asymptotic value of firmness depending on the genotype, a value which Andrade et al (2005) have taken to be zero; A is the initial value of the firmness in the zero time, discounted from B; and $t\tfrac{1}{2}$ is the post-harvest half-life, a characteristic that can be used for selecting genotypes with greater storage capability.

At present, the tomato cultivars available on the Brazilian market do not have ripeness-marking gene any more, as was the case, for example, with the Kada cultivar. Consequently, defining the "breaker" ripeness stage make the use of the method difficult, as it has been employed (Andrade-Junior et al, 2005). Equation 1, however, may be used only with data taken after ripening begins. With this method, the beginning of ripeness is estimated at the moment when the fruits begin to lose firmness. As a result, the measurements for estimating $t\tfrac{1}{2}$ with equation 1 are only those that effectively were made after ripening began. The data obtained before this are a physical estimate of the pre-climacteric life of the fruits harvested, which can be confirmed by reading the concentration of ethylene in the internal atmosphere. The parameter days of pre-climacteric life thus estimated has not been used in vegetable improvement programs yet.

The flattening technique has been used for determining the loss of firmness during ripening of guava and mango. In the case of vegetables like egg-plant and sugar beet (Scientia AGrícola, v. 56, p. 1045-1050, 1999) and carrot (Bragantia, v. 59, p. 7-10, 2000; Horticultura Brasileira, v. 21, v. 597-600, 2003), the flattening method has been used for determining the loss of firmness caused by transpiration and the consequent dehydration of the organ. Measurements of turgescency of fruits and vegetables by the flattening technique have also been useful in logistics for determining the maximum height of packages and stacks of stored bulk fruits and vegetables (Horticultura Brasileira, V,21, p. 704-707, 2003). In spite of the varied applications of the method, there are still no commercial instruments for making these measurements of turgescency.

In order to determine hydric stress in plants, there are other types of techniques that involve compressing plant tissues. Shayo-Ngowi & Campbell (Agonomy Journal, v. 72, p. 567-568, 1980), for example have developed a "hydraulic press" for estimating the tension with which water is withdrawn from cell walls and in the xylem vessels of leaves and segmented tissues. For this type of measurement, segments, typically with an area of 25 $mm^2$ and with thickness of up to 3 mm, are compressed under the transparent glass plate until the sap begins to pour through the bundle of vessels. According to Eldrege & Shock (American Potato Journal, v. 67, p. 307-312, 1990), the "hydraulic press" method exhibited a high correlation with the water tension measured with the Scholander pressure chamber (Sholander et al., Proceedings of the National Academy of Science, USA, v. 52, p. 112-119, 1964) in potato leaves. However, this author clarifies the lack of theoretical basis for employing the "hydraulic press", a drawback that has been partly overcome with the developments presented in the papers by Calbo et al. (Annals of Botany, v. 76, p. 365-370, 1995) and Calbo & Nery (Brazilian Archives of Biology and Technology, v. 44, p. 41-48, 2001). In order to measure the turgor pressure in leaves with thickness ranging from 0.05 mm and 2 mm, a system called Wiltmeter was developed in 2007, which uses blockage of a flow of blown air with pressure on the order of 5 kPa, on a porous and rigid plate. The system is based on the criterion of flattening the leaf to estimate the cell turgor pressure in this organ (PI0705830-6). The pressure read is that applied to push the leaf against the flattening plate with a porous element, with the aid of a flexible membrane, which is inflated with water applied with a plunger. As a result, the Wiltmeter is not suitable for measuring cell turgor pressure in bulky organs like fruits, roots and stems. The error with which the pressure applied by the membrane is transferred through the leaf as far as the flattening plate, where the air flows between the leaf and the plate, increases with the thickness of the leaf, or slice in the case of sliced organs, so that the reading should be made preferably on samples with thickness lower than 2 mm. the system of PI0705830-6, by applying compression from one side with an inflatable membrane and reading the air permeation between the plate and the leaf on the other side, is not suitable for reading the firmness of voluminous organs of more or less cylindrical or ellipsoidal shapes, nor is it suitable for applications related to automation of the handling of irrigation water.

Also for leaves, Zimmermann et al. (J. Expt. Bot. v 59, p. 3157-3167, 2008) have developed a brace with a pressure transducer inserted under a silicone layer for measuring the turgor pressure. In this instrument, an electric pressure signal is generated from the variations in volume and turgor pressure of the leaf. For measurement, the leaf is pressed between two planar plates. The first plate is rigid and the second one is covered with silicone rubber and contains internally the pressure transducer, the signal of which is always a fraction of the pressure applied in the leaf. According to the authors, this instrument enables continuous acquisition of turgo-pressure data of leaves with different thicknesses. In the Zimmermann et al. system, the pressure of the leaf is calculated by a non-linear equation, the definition of the parameters of which involves approximations. Additionally, the sensor exhibited delay in response of up to 4 hours as compared with the readings of cell turgor pressure made with the cell pressure probe by the authors themselves.

For the time being, turgo-pressure measurements have not been used to handle irrigation, except indirectly, as by reading the variation in the diameter of stems and fruits with instruments analog to the Alvim dendrometer (Alvim, Turrialba, v. 25, p. 445-447, 1975), but provided with an electrical connection. In the case of dandrometers, the turgor pressure and the growth are two variables that are summed to determine the stem diameter. Thus, since the dendrometer does not separate the effect of the cell turgescency pressure, it does not enable direct decisions referring to the correct moment of irrigating. Instruments that can measure turgor pressure in a continuous manner and without interactions with the growth are not yet available for use in handling irrigation water. Additionally, there is no system available for automating irrigation systems that is based exclusively on the reading of dendrometric instruments.

About the dropping system and drippers, it is important to point out that there is no description of drippers that are directly actuated by reducing the cell turgor pressure of stems and other plant organs. The dropping systems described hereinafter were developed mainly from 1970, in order to apply water close to the plants with a view to save water, prevent erosion and reduce leaching of mineral nutrients. Some of the determined characteristics of the applicability of the dropping systems were mentioned by Gillad in 1972 (GB 139200), when developing injected-plastic drippers with a labyrinth for the water dissipating pressure without the as thin and elongate orifices as they are used in microtubes. This principle was improved by Gomey in 1987 (U.S. Pat. No. 4,655,397), when he introduced the vortex dripper. However, only in part do these improvements meet the ideality criteria which, according to Gillad, are: a) uniform and low flow-rate dropping; b) non-clogging of the drippers, even without the use of sophisticated water-filtering systems; c) small dropping units to facilitate transportation and mounting.

Hardison, in 1975, (U.S. Pat. No. 3,510,500) describes a drip irrigation system for applying soluble mineral nutrients, fertirrigation. In this system, with at least two sand filters the irrigation could continue while one of these filters was being cleaned by backwashing. The use of these dripping systems with the option of applying water and fertilizers has brought valuable agricultural possibilities, but has increased the problems of dripper clogging. In order to solve this problem, drippers with flexible components have gained importance. One early type of these drippers is the one described by Mullett in 1977 (U.S. Pat. No. 4,037,791), which made used of a collapsible microtube of small diameter through which a copper wire passes for water to flow through. In this system, the drippers are placed inside a hose, the increase of pressure in which compresses the microtube proportionally, because the pressure inside the hose is higher than the atmospheric pressure at the outlets of the collapsible microtube. Thus, in the compressed microtube, the flow-rate is kept, whereas the work pressure varies. The inserted copper wire in this system inhibits the growth of roots or algae and reduces clogging. Among the drippers that are less susceptible to clogging are those with anti-siphoning mechanism, like that developed by Ruskin in 2006 (US 2006255186), which also contains a flexible membrane for sealing water leakage when the flow of water is closed for irrigation. In this way, one prevents water tension developed in some parts of the hose from causing suction of soil particles through the dripper, which causes clogging. These systems with flexible or collapsible components, however, have not been used so far for controlling the flow-rate of water dripping out of drippers according to the variations of the cell turgor pressure.

The present invention deals with a system for making use of the dynamic and elastic shape with which the volume and the cell turgor pressure of plants vary with the state of hydration to construct instruments for reading cell turgor pressure in voluminous organs like fruits and stems, and drippers that automatically meet the hydric demand for irrigated crops. The turgor pressure and the elastic variations of the volume of the tissues caused by the state of irrigation of the plant are used for pressing, deforming and actuating the pressure-measuring and flow-rate controlling device.

SUMMARY OF THE INVENTION

Figure 1:
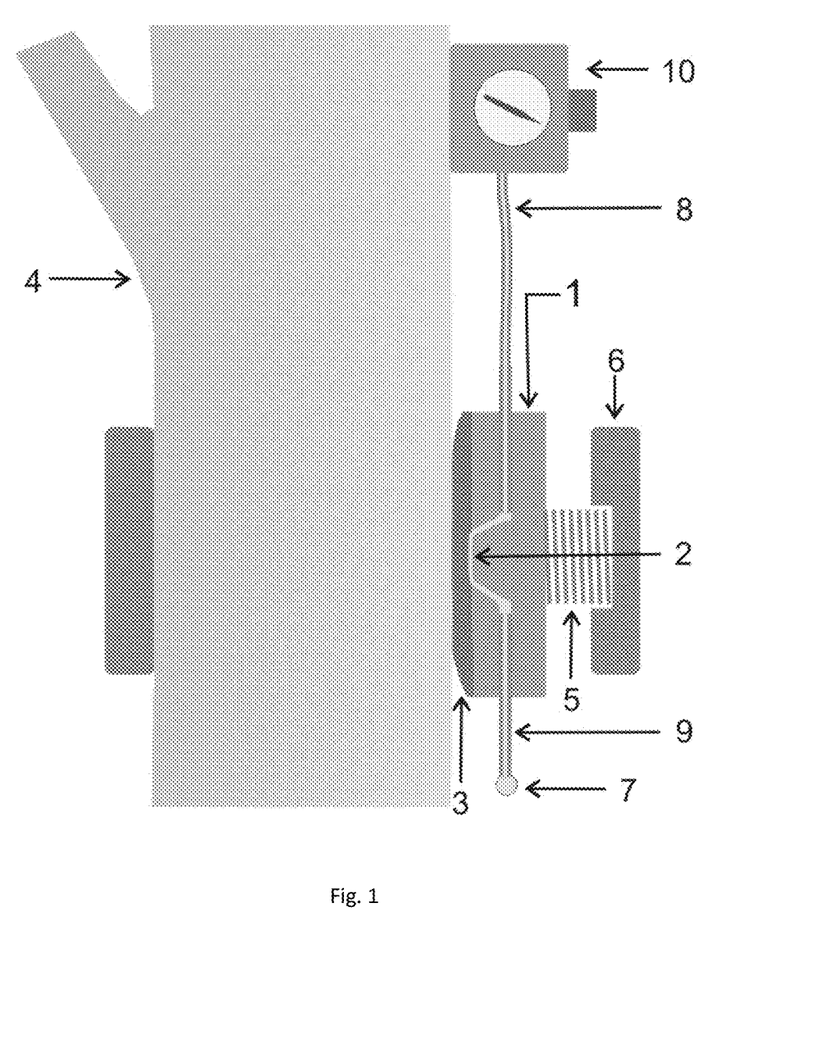
FIG. 1: a dripper with water flow-rate controlled automatically by the pressure in elastic tissues of the plant and that releases water when the pressure in the plant tissue becomes lower than the water pressure adjusted on a pressure regulator.
Figure 2:
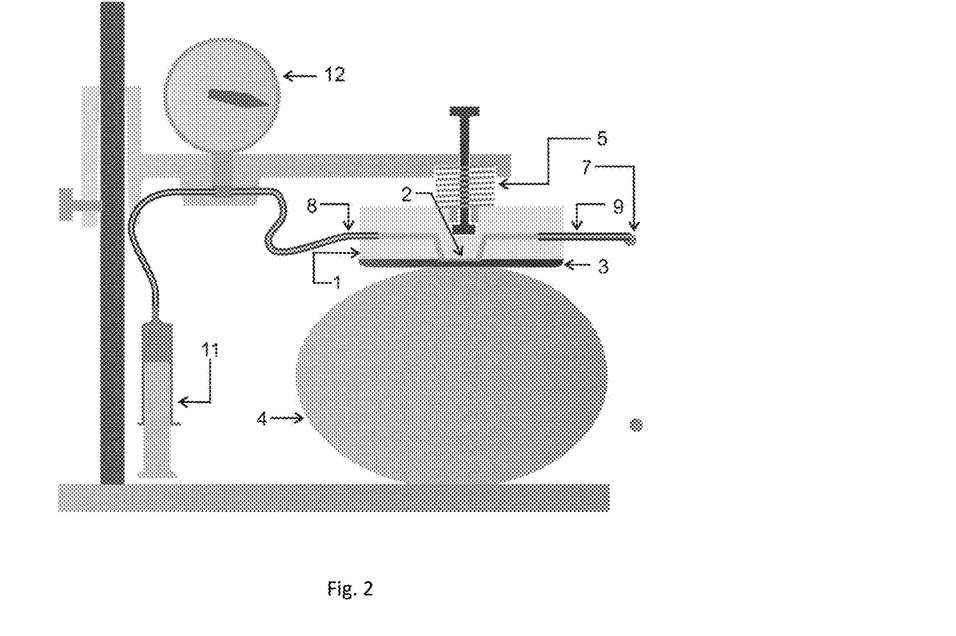
FIG. 2: a system for measuring the cell turgor pressure similar to the system of FIG. 1.

In order to function as an automatic dripper, the system of this invention takes advantage of the elasticity and pressure of the plant tissues by using, as can be seen in FIGS. 1 and 2, a flattening plate (1), covered by a flexible membrane (3), which contains a fluid layer (2), which upon being compressed obstructs the flow of the same fluid, typically water or air. Irrigation-water dripping begins when the adjusted pressure of the water in the tubing, by means of a pressure adjuster (10), becomes higher than the pressure of the plant tissues, that is, when the plant would begin to have difficulty in absorbing water from the soil or from the substrate in an amount sufficient to keep the cell turgor pressure. A similar system may also be used for constructing simple instruments for measuring the cell turgor pressure of organs, plants, as can be seen in FIG. 2, in which the pressure is applied with the aid of a plunge (1) and is read with a pressure transducer (12). The flattening caused on the fluid membrane (2) by compressing the organ against the membrane (3) prevents passage of fluid until the applied pressure exceeds the cell turgor pressure and causes flowing, a situation in which the reading of the turgor pressure is taken. The width of the fluid layer (2) may be adjusted to meet applications on organs and other irregular structures, even when they are diminutive. For continuing acquisition of date, the fluid layer (2) may be linked, on the one side, to a pressure transducer (12) and, on the other side, to a cover (FIGS. 3-13). The area of the flattening fluid layer (2), even in this case, should be elongate in order to facilitate accommodation on irregular organs. In after-harvest, the system can be prepared for portable use or else secured to a pedestal, on which the compression device aids with stability of reading.

DETAILED DESCRIPTION OF THE INVENTION

The dripping control system illustrated in FIG. 1, and the turgor pressure measuring system illustrated in FIG. 2, of this invention take advantage of the volumetric elasticity of the plant tissues, that is to say, the fact that the volume of the organs increase with the increase in the cell turgor pressure and of the dynamic availability of water in the tissues.

In FIG. 1, a storage plate (1) serves for the squeezing force applied by a spring (5) supported on a brace (6) to cause the application of pressure of the plant tissue onto the membrane (3) that coats the plate (1). In this way, the fluid layer (2) of small width, kept under the flexible membrane (3), is compressed and flattened by the plant organ (4), constituted by parenchymatous tissues, that is, composed of unspecified and soft cells. In FIG. 1, the pressurized area of the membrane (3) depends on the force applied by the spring (5) and on the organ pressure, which is, at the most, equal to the cell turgor pressure itself, when the cells have thin walls. While the organ (4) pressure is higher than the pressure with which the water is forced through the inlet tube (8), no dripping (6) takes place. The passage of the water through the outlet tube (9) does not take place in this case because the fluid layer (2) is completely flattened. The material that constitutes these tubes may be capillary one of copper, steel, glass or any other rigid material.

As the availability of water in the soil decreases and the transpiration causes decrease in the cell turgor pressure, the adjusted water pressure in the pressure regulator (10) may exceed the pressure of the plant onto the membrane and the water dripping is started. Said pressure regulator may be those widely available on the market for controlling gas and liquid pressure, the single-stage ones being intended for applications without much accuracy, the double-stage ones being intended for application with greater accuracy, the two types being applicable to the invention. In this case, the dripping operation energy is supplied by the water pressure itself, adjusted on the pressure regulator.

The fluid layer (2), preferably elongate and narrow, which is flattened, of the system for measuring cell turgor pressure enables the passage of fluid whenever the pressure applied is higher than the flattening pressure exerted by the organ (4). This dominance of the length over the width is important for the following reasons: a) the volumetric variations of the organ involved in the measurement should be diminished, so as to enable rapid control of the water flow-rate, requiring only imperceptible motions of water inside the plant organ; b) it imposes a maximum limit on the flow rate; and c) it facilitates miniaturization of the dripper, so that it can be used even on the same of small ornamental plants and vegetables.

The flattening layer (2), generally speaking, may be reduced to a mere orifice, the inlet (4), on which the membrane (3) rests. On this membrane the flattened organ pressure allows the fluid to escape when the regulated water pressure exceeds the cell turgor pressure of the organ. Another specification is to convert the outlet tube (9) into a mere outlet opened under the membrane. Thu, the fluid will now escape freely. This simplification is useful on hydrophyte plants that bear well the direct and continuous contact with free water.

In FIG. 2, one observes the operation system with the aid of a plunger (11), or syringe, in the case illustrated, of manual application. The organ (4) in the example is pressed against the transparent plate (1) on a simple stationary securing frame, with pressure by spring (5), which is equivalent to the brace system illustrated in FIG. 1. For the purpose of reading, one increases the pressure on the syringe until the water begins to pass or dripping starts, instrument of FIG. 2. This lower pressure that causes the passage of fluid is the measurement of the turgor pressure of the plant organ, the reading being made on the pressure transducer (manometer).

The length and chiefly the width of the layer (2) with fluid, for flattening, of the automatic dripping system shown in FIG. 1 and of the system for measuring the turgescency of fruits and vegetables illustrated in FIG. 2, may be miniaturized and may be easily diminished to a width of 0.10 millimeters, a width that is on the magnitude order of the length of an ordinary parenchymatous cell. Bigger miniaturizations are conceptually possible.

The flattening plate (1) may be produced from plastic, which may be rigid PVC, transparent acrylic or polyacetal. The dimensions thereof may vary, depending on the dimensions of the sample. A possible recommendation of the maximum size of the plate, of rectangular shape, would be, at most, 4-5 cm in height per 1.5 cm in width, because above this size there is the need for a spring with a high constant K, which would result in using a hard spring. In terms of minimum dimensions, the plate of 1 cm in height per 0.5 cm in width was tested, but conceptually this size may be diminished if there is an interest therein. This plate may be secured to the spring system (5) either by fitting (FIG. 1) or by means of a pin P (FIG. 2). The membrane (3) may be produced, for instance, by deposition of neutral-cure silicone onto the plate (1), and may range from 0.5 to 5 mm. the fluid layer (2) for flattening may be formed with the aid of a nylon or polyethylene ribbon, to which the acetic cure silicone does not stick and which, therefore, may be pulled and removed as soon as the membrane is cured. The construction, as well as the thickness of the membrane, is not dependent on the application onto stems or fruits and vegetables. The fluid layer (2) for compression thus formed has width and thickness equal to that of the ribbon that is used as a manufacture mold.

For measuring whole fruits and vegetables, the width of the layer (2) may range from 0.1 to 4.0 mm. for applications such as dripping systems, shown in FIG. 1, the width of the layer (2) for flattening should be as close to the limit (0.10 mm) as possible, so that it can limit the dripping rate in the application in terms of plant, soil and climate, as the case may be. Typically the width and the length of the flattening layer (2) should be calculated so that the water flow rate will be lower than 4 liters per hour, under an adjusted water pressure difference of 30 kPa.

The elongate form of the layer (2) and that the organ needs to flatten only a part of this sensitive layer lengthwise facilitates the use of the dripping control systems of FIG. 1 and the systems for measuring the turgor pressure of fruits with the similar fluid pouring of FIG. 2. Besides facilitating the use, this enables measurements on small organs such as the stems of vegetables and ornamental plants, and on the surface of irregular fleshy fruits, like certain types of cucumber or carrot roots.

Closed System

Figure 3:
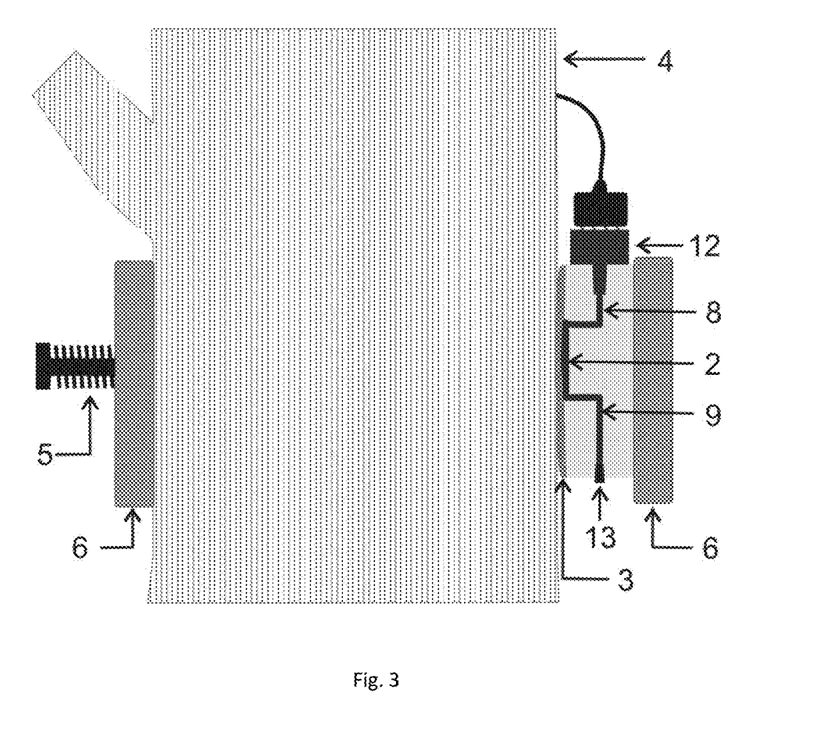
FIG. 3: a closed system for measuring the turgor pressure in stems with dentroturgometers.

The system illustrated in FIG. 3 for measuring cell turgor pressure, technically may be called dentroturgometer, since this is an application for use on stems. In this application, the plate (1) compresses the membrane (3) and, as a result, the fluid layer (3), which is flattened by the pressure of the organ pressed by the brace system (6), with a spring (5). Unlike what was described in FIGS. 1 and 2, in FIG. 3 the system is closed with a cover (13) on the side of the outlet tube (9), and connected to a pressure transducer (12), which may be either analogous (the observer will write down the measurements manually) or electronic (there will be a need for electric energy or batteries), on the side of the inlet tube (9). The fluid contained in this system is preferably mineral oil, which will tolerate exposure to ultraviolet light. The pressure of the organ (4) causes only a partial flattening on the layer (2), which will enable continuous reading of the turgor pressure. The turgo-pressure data obtained with the closed system of FIG. 3 can be used for ecophysiology studies and for applications of irrigation handling. The dendroturgometer has a differential aspect of measuring the turgor pressure separately. In this way, it is ideal for handling irrigation, since it does not require separation of the effects of the turgor pressure and of the growth, as is the case with ordinary dendrometers. Therefore, this is a system that can be used for handling irrigation, even on plants in the phase of active growth.

Evidently, the system of FIG. 3 may be mounted on a stationary support equal to that illustrated in FIG. 2, for after-harvest application. Alternatively, the system of FIG. 3 may be slightly modified for the construction of a portable instrument, shown in FIG. 4, on which the force for reading the pressure of the fruits is applied manually by holding the cable (15), which replaces the brace (6) and spring (5) system, for measuring turgor pressure with the aid of a pressure transducer (12) and a reading device (14). In this case too, the outlet tube (9) is closed with the cover (13), and the closed fluid in the system between the membrane and the inlet tubes (8) and the outlet tubes (9). Between the fluid inlet tubes tested, one employed tubes with 0.1 mm in inner diameter (for applications on small stems or small groups of cells), to 1-2 mm inner diameter, at the most (for bigger stems or fruits and vegetables).

Figure 4:
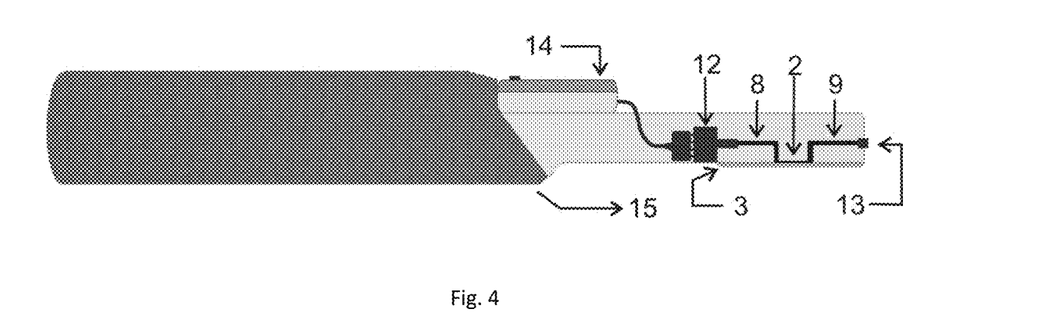
FIG. 4: a portable system for measuring the turgor pressure.

In after-harvest, the portable systems are practical and enable mobility, but better results are achieved in stationary systems, in which the pressing force is provided by systems with spring (5), as shown in FIG. 2), which evidently may be used with a reading system with closed fluid, as shown in the portable system of FIG. 4. The portable instrument, on the other hand, is useful in field and retail applications, since it may constitute a new method, so that the consumer will know about the firmness of the product without handling it. The reading with a cleaned portable instrument can certainly be classified as a good agricultural practice.

In addition to the reading stability, lower on portable instruments, as shown in FIG. 4, it is also important to consider that the cell turgor pressure may vary with the position on the surface of the organ. On tomato fruits of the cultivar "Kada Gigante" (Giant Kada), for example, ripening begins at the distal tip and the process advances toward the insertion of the peduncle, which is a typical placing standard along the length of the half-ripe fruits.

In the measurements on the sensor with fluid in the closed system of FIGS. 3 and 4, the positioning of the organ (4) is more difficult and needs to be made carefully, so that the elongate flattening layer (2), under the membrane (3), will be wholly pressed by the organ. For this reason, the elongate shape of the flatting layer (2) with fluid is important to facilitate the positioning of the dendroturgometers, illustrated in FIG. 3, and of the firmometers for after-harvest use, as shown in FIG. 4, since it facilitates said adjustment of position on elongated or irregular plant organs.

The pressure reading system of FIG. 3 is automatized, electronic. One uses as a source of electric energy, such as a battery for supplying energy to the commercial pressure transducer, which may be of varied types (example, piezoelectric transducer or resistive extensometer of the Strain Gauge type).

System without Fluid

Figure 5:
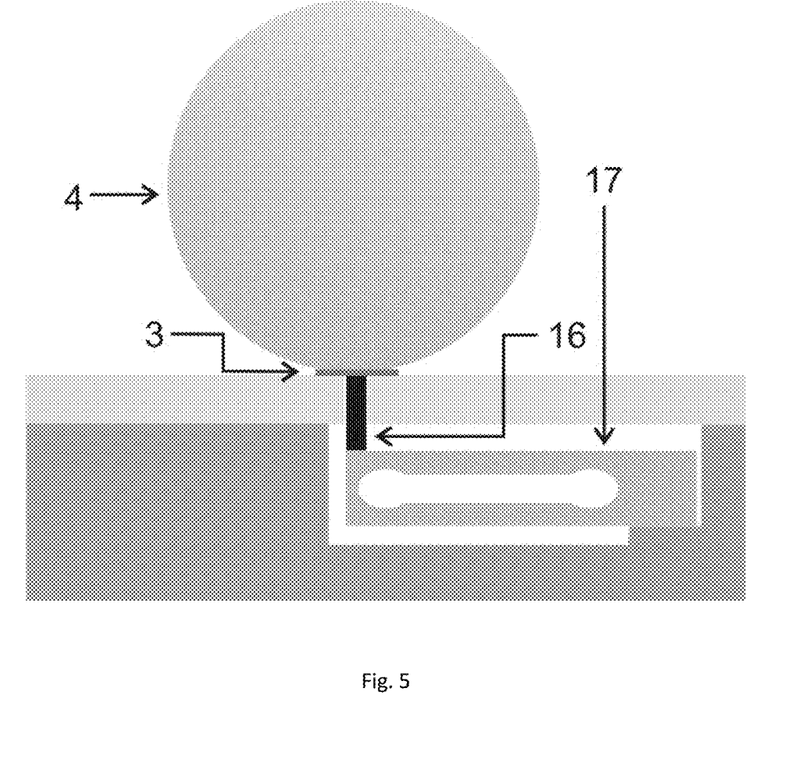
FIG. 5: a system with moveable rod that enables more accurate reading of the cell turgor pressure when the organ is pressed onto the whole coplanar surface of the movable cylinder.

In FIG. 5, one illustrates a fluid-less system for taking advantage of the hydric elasticity in measuring cell turgor pressure. The system has a movable rod (16), preferably with an elongate cross-section, which, on the one side, is supported on the force transducer (17) and, on the other side, has a plane face kept at a level virtually equal to that of the external plane of the plate (1), under the flexible membrane (3). The rod not only transfers the pressure of the organ (4) to the force transducer (17), but also prevents the entry of impurities, which might lock the movement and the reading of force, mediated by the rod (16).

As in the cases of the systems of FIGS. 3 and 4, the whole cross section of the rod (16) under the membrane needs to be compressed by the pressure of the plant organ. Generally speaking, the stem may be replaced by other force measurement systems that can measure the cell turgor pressure, while undergoing microscopic deformation, as is the case in various load cell systems, as for instance, those based on the resistive piezotechnology.

Generally speaking, firmometers prepared with the stem of FIG. 5 are more sensitive to space orientation and to vibrations than systems with fluids. This, however, may be lessened, if the stem is removed from the system and the reading is made directly on the solid-state force and pressure sensor.

By using load-cell-type force transducers (17), as illustrated in FIG. 5, the pressure of the organ (4) is achieved by dividing the measured force, discounting the stem weight, by the cross-sectional area of the stem.

Physiological Considerations

The cell turgor pressure determines the freshness appearance of the organs highlighted and may be decreased by dehydration, ripening and sencescence. The thickness of the cell wall, and in lesser proportion the intercellular gas volumes cause the measurements of the instruments of this invention to be slightly smaller than the cell turgor pressure. From the point of view of vegetable physiology, a useful aspect is that the intercellular volumes in the flattened region are diminished, but they are not completely annulled, which enables measurement of the turgor pressure for long periods of time, without causing hypoxia damages to the tissues studied, for instance, as in the dripping application of FIG. 1 or on dendroturgometers of FIG. 3.

The compression force applied for measurement with the instruments of this invention should be sufficient to flatten the whole layer (2) under the membrane in the applications with pressure transducer of FIGS. 3 and 3, and under the whole transverse face of the rod (16) of the system illustrated in FIG. 5. Thus, the force for an area of 0.10 cm$^2$ on organs with limit turgor pressure of 8 kgf/cm$^2$ is calculated by multiplying the limit turgor pressure by said area. In this case, one obtains that the force necessary to flatten an area by at least two times as large as 0.10 cm² is 1.6 kgf.

The mounting of FIG. 3 is ideal for following the turgor pressure of plants in the field, for ecophysiology studies and for biological assessment of methods for handling irrigation based on variables of the soil and of the atmosphere. Additionally, the presently proposed system can also be used for applying the deirrigation-deficit concept, which is a technology in development and for which still there is no adequate plant sensors on the market. The proposed system tends to function better on monocotyledoneous plants and herbaceous plants that tend to have soft dermal tissue (15), being suitable for application of the system of this patent.

In FIGS. 3, 4, and 5, the layer (2) has a minute width for dripping operation on herbaceous plants with a diameter larger than 4 millimeters and also for laboratory measurements, for instance, on roots and ribs. For the dripping applications of FIG. 1, it is advisable for the flattening layer (2) to have a diminutive area smaller than 0.025 mm² and length, for example, of 4 to 15 mm. In this way, one may apply water with low flow rate, preferably less than $4^{Lh-1}$. If the flattened area is of 1 mm per 4 mm and if on the organ to be measured the turgor pressure rises up to 1.0 MPa, then the spring (5) should exert a force ranging from 0.4 to 0.6 kgf. In the dripping systems of FIG. 1 the flattening does not need to take the whole length of the layer (2). However, the flattening of the sensor by the organ should occupy a number of times the width of the layer (2), so that it can effectively obstruct the flow of water, whenever the turgor pressure is kept higher than the water pressure adjusted on the pressure regulator (10).

An equally relevant issue in this invention is the estimation of the tissue of the organ that is compressed. This volume depends on the geometry of each organ. However, one can achieve an approximate idea by imagining the flattening of a spherical cap in which the radius of the organ is the radius of this cap.

The volume of a spherical cap is represented by:

$$V = 7\pi\, h(3a^2+h^2)/6 = 7\pi\, h^2(3R-h)/3 \qquad \text{eq. 2}$$

wherein V is the volume, h is the height of the flattened spherical cap a is the radius of the flattened area and R is the radius of the organ. From equation 2 it follows:

$$h^2 - 2Rh + a^2 = 0 \qquad \text{eq. 3}$$

If $a^2$ in the case considered is equal to a fourth of the product of 0.1 cm per 0.4 cm, then if R is equal to 1 cm, one calculates that the height of the flattened cap h is 0.005 cm and that the volume of the flattened tissue cap V is of 79 nL. This deformation is of about two tenths of a thousand of the organ volume, which presumably represents a diminutive and reversible biological stress in view of compression stresses that are thousands of times higher than necessary in earlier studies, in order to cause detectable physiological effects on the ripening of the tomato. If the area flattened by the spring doubles while the plant loses turgescency until the irrigation is triggered, then the flattened volume of the spherical cap that increases in the proportion of the square of the flattened area and that, in the case under consideration, would pass from 79 nL to 316 nL, according to equations 2 and 3.

With the outlet tube (9) dosed by a cover (13), the fluid is pressurized according to the cell turgor pressure. In FIG. 3, just as in the embodiment of FIG. 1, besides having strength enough, the thickness of the membrane (3) should preferably be on the order of the broadness of the flattened layer (2), and the membrane material should have a volumetric elasticity module of at least 10 MPa, which is met by various types of flexible materials, such as silicone rubber, for example.

In order to make the reading easy, the system mounted with a pressure transducer illustrated in FIGS. 3 and 4 may have a narrow flattening area with broadness on the order of 0.4 mm and length on the order of 4 mm. The total volume under the flattening area (1) thus configured is of 160 nL. For reading pressures of up to 1 MPa on a pressure transducer connected to this flattening area, the larger tolerable volume of a fluid with compressibility of 0.00078 Mpa⁻¹ is calculated on 0.205 mL in the limit situation in which the whole fluid volume under the flattening layer (2) is compressed on the pressure transducer itself. Thus, since the fluid additionally has thermal expandability with magnitude on the order o. 0.00078° C., in this system for greater safety, it is advisable to maintain the dead volumes inside the transducer (12) and the inlet tubes (8) and outlet tubes (9) at less than 0.05 mL.

In order to measure this system, the pressure in the organ could rise up to 1.0 MPa. Thus, if the flattening ellipsoid has a smaller diameter equal to 2 mm and the larger diameter equal to 8 mm, then either the spring force in FIGS. 1, 2 and 3, or the force of the hand that holds the cable (15), necessary to compress this specified surface area or the organ on the sensor is of 1.25 kgf, in the specified condition.

Gauging and Marking

Figure 6:
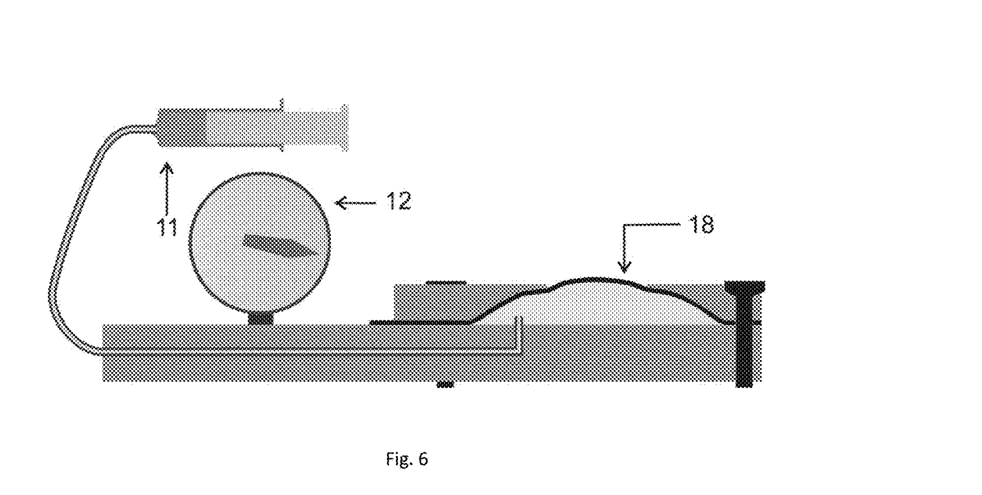
FIG. 6: a system with an inflatable membrane for gauging the instruments of this invention and other applications of non-destructive measurement of the cell turgor pressure.

The embodiments of the system of this invention do not require calibration, but they may be subjected to different gauging to verify the correct functioning. For instance, assessments may be made through comparisons with the pressure probe, with the flattening technique or, preferably, by compressing the sensor against an elastic membrane (16) of a gauge illustrated in FIG. 6, the internal pressure of which is adjusted by pressing a plunger (11) and read on a pressure transducer (12). The pressure applied with the gauging system of FIG. 5 should be very close to the readings obtained with the instruments illustrated in FIGS. 1, 2, 3 and 4, which are pressed against the gauge. In the use of the gauge, one should be careful not to apply pressure before having the gauging instrument firmly secured, so as not to cause damage to the elastic membrane (16), which is used for applying gauging pressures.

Besides the possibility of gauging, it is necessary, for comparative purposes, to have an idea of the magnitude of the turgor pressure values on various organs. Thus, it is common to achieve values of about 6 kgf/cm² for carrot, 5 kgf/cm² for potato and onion, and values lower than 2 kgf/cm² for leaves. In a general way, the turgor pressure in growing order of newly harvested and well hydrated organs is: of tuberous roots (5 to 10 kgf/cm²), tubercles (4-7 kgf/cm²), unripe fruits (1.5-4 kgf/cm²), leaves (1-3 kgf/cm²) and ripen fruits (0.2-1 kgf/com²), respectively. In all the cases, turgor pressure values that approach zero indicate that the product is either dehydrated or is already senescent and unsuitable for consumption. Normal homeostatic values of turgor pressures are indicative of quality and acceptability of the product. These homeostatic values are usually within a range that goes from a lower threshold of commercial acceptability, which requires experimental determination and that is typically of magnitude higher than 40 kPa, to a turgor pressure of three or more times as high that achieved at the time of harvesting.

Applications on After-Harvest

Figure 7:
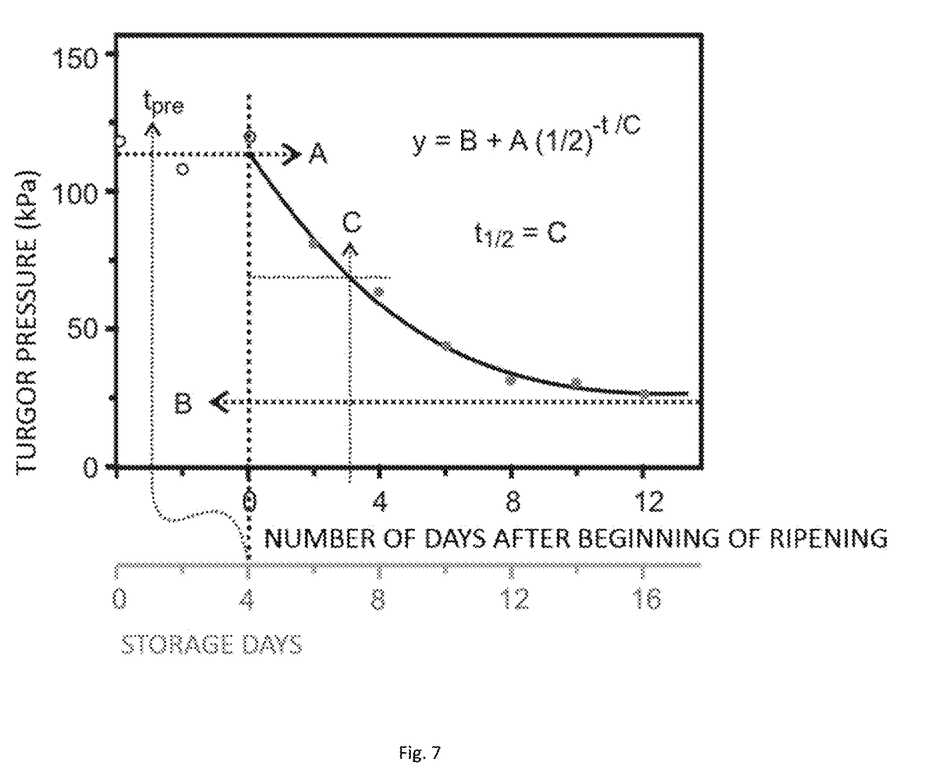
FIG. 7: after the period of maintaining the firmness of tomato fruits in a pre-ripening phase (empty circles), an adjustment of a time constant called after-harvest half-life there of takes place; the data enable one to determine pre-ripening storage days ($t_{pre}$), after-harvest half-life (A) and basal turgor pressure B.

FIG. 7 illustrates the typical variation in the turgor pressure with the mathematic expression that represents it, after the tomato fruit starts ripening (full circles), according to readings made always in the same area on the fruit surface. Under stable temperature and high moisture (>90%), this curve serves to stimulate the after-harvest half-life. The data represented by empty circles in this curve are not adjusted, but are useful to define the number of storage days before the fruit begins to ripen, induced by ethylene.

For the measurement on flat organs or thick slices of more than 3 mm thickness or with ribs, the plate (1) should be slightly convex and the flattening layer (2) should have a broadness of less than 0.4 mm, so that one can deform the structure only along a strip having thickness of about 1 or 2 mm, or even less.

For applications to fruits and vegetables in retail, the system may be a portable one, mounted on a flat plate (1) with a reader (14), as illustrated in FIG. 4, this portable instrument is manually pressed against the commercialized organs. An exposed table with firmness values will give the buyer a comparative idea of the turgescency of the product. Measurement with the firmometer of FIG. 4 is an alternative to discourage touching fruits and vegetables during the purchase, a practice that is not usual in Europe and in the USA, where the hygiene standards are socially applied at a better level.

Non-Ideal Situations

The system of FIG. 3 is known for use on phytomonitoring, since it enables continuous measurement of the turgor pressure on the stem, instead of mere measurements of variations in diameter, made with an ordinary dendrometer. This is an important alternative, since the turgor pressure is a physiological variable of simple interpretation ad that enables one to define threshold values below which irrigation should be applied to a plant. In these situations, it is common for the sterns to have only approximately the properties advocated for carrying out valid measurements.

On these stems, however, a few geometrical irregularities caused by minor sclerification, can be eliminated, for instance, when they involve soft patterns, such as trimming. In cases like this, one may use a pre-treatment of the area with a neutral-cure silicone layer with thickness sufficient to fill said irregularities, so that in this way it can be adequately flattened by the brace (6) and spring (5) system.

The invention claimed is:

1. A pressure measuring and flow-rate controlling device comprising:
    a flattening plate comprising a fluid cavity in which a fluid layer is established;
    a flexible contact membrane provided on the flattening plate and in direct contact with the fluid cavity;
    a support member configured to secure the flattening plate against a sample;
    a pressure adjuster;
    an inlet tube configured to intercommunicate with the fluid cavity; and
    an outlet tube configured to intercommunicate with the fluid cavity,
    wherein the pressure adjuster is configured to control a flow rate of a fluid passing through the fluid cavity based on cell pressure of the sample.

2. The pressure measuring and flow-rate controlling device according to claim 1, wherein the support member comprises:
    a spring; and
    a brace.

3. The pressure measuring and flow-rate controlling device according to claim 1, wherein in response to the cell pressure of the sample increasing, the flattening plate and the flexible contact membrane closes the fluid cavity.

4. The pressure measuring and flow-rate controlling device according to claim 1, wherein in response to the cell pressure of the sample decreasing, the flattening plate and the flexible contact membrane opens the fluid cavity.

5. The pressure measuring and flow-rate controlling device according to claim 1, wherein the outlet tube further comprises a dripping end.

6. A pressure measuring and flow-rate controlling device comprising:
    a flattening plate comprising a fluid cavity;
    a flexible contact membrane provided on the flattening plate and in direct contact with the fluid cavity;
    a support member configured to secure the flattening plate against a sample;
    a pressure adjuster;
    an inlet tube configured to intercommunicate with the fluid cavity; and
    an outlet tube configured to intercommunicate with the fluid cavity,
    wherein the pressure adjuster comprises:
    a pressurization plunger; and
    a manometer connected to the inlet tube.

7. The pressure measuring and flow-rate controlling device according to claim 6, wherein the support member comprises:
    a stationary securing frame;
    a spring; and
    a pin.

8. The pressure measuring and flow-rate controlling device according to claim 6, wherein in response to the cell pressure of the sample increasing, the flattening plate and the flexible contact membrane closes the fluid cavity.

9. The pressure measuring and flow-rate controlling device according to claim 6, wherein in response to the cell pressure of the sample decreasing, the flattening plate and the flexible contact membrane opens the fluid cavity.

10. The pressure measuring and flow-rate controlling device according to claim 6, wherein the outlet tube further comprises a dripping end.

* * * * *